United States Patent
Bonnevie et al.

(10) Patent No.: US 6,510,729 B2
(45) Date of Patent: Jan. 28, 2003

(54) DEVICE FOR DETERMINING THE CORROSION OF THE GRINDING BODIES IN A ROTARY MILL

(75) Inventors: Michel Bonnevie, Bovesse (BE); Louis Boulanger, Tiege (BE)

(73) Assignee: Magotteaux International (BE)

( * ) Notice: Subject to any disclaimer, the term of this patent is extended or adjusted under 35 U.S.C. 154(b) by 0 days.

(21) Appl. No.: 10/000,205

(22) Filed: Nov. 1, 2001

(65) Prior Publication Data

US 2002/0078738 A1 Jun. 27, 2002

(30) Foreign Application Priority Data

Nov. 6, 2000 (BE) .......................................... 2000/0708

(51) Int. Cl.[7] .............................................. G01N 17/00
(52) U.S. Cl. ........................... 73/86; 204/404; 324/700; 422/53; 451/85; 241/21
(58) Field of Search ............................... 73/86; 422/53; 324/700; 204/404; 451/85, 120, 140, 142, 178, 209, 324, 328, 460; 241/21, 27, 87.1, 88, 111, 117, 170, 184, 273.1, 273.3, 299, 183

(56) References Cited

U.S. PATENT DOCUMENTS

| | | | | |
|---|---|---|---|---|
| 2,987,672 A | * | 6/1961 | Marsh et al. ................ 324/443 |
| 3,607,606 A | * | 9/1971 | Beninga ..................... 428/325 |
| 3,942,546 A | * | 3/1976 | Radd et al. .................... 137/93 |
| 3,955,766 A | * | 5/1976 | Chang ......................... 241/114 |
| 4,412,174 A | * | 10/1983 | Conlon et al. ............... 250/303 |
| 4,703,254 A | * | 10/1987 | Strommen ................... 204/404 |
| 5,036,287 A | | 7/1991 | Serwatzky ................... 324/700 |
| 5,150,065 A | * | 9/1992 | Luna ........................... 324/700 |
| 5,403,550 A | | 4/1995 | Wietek .......................... 422/53 |
| 5,712,559 A | * | 1/1998 | Moore et al. ................ 204/404 |
| 5,752,665 A | * | 5/1998 | Wason ......................... 241/183 |
| 6,027,057 A | * | 2/2000 | Miles .......................... 241/182 |

FOREIGN PATENT DOCUMENTS

| | | | |
|---|---|---|---|
| GB | 1 586 822 | 3/1981 | |
| WO | WO 199325310 | * 12/1993 | ........... B02C/17/22 |

* cited by examiner

Primary Examiner—Hezron Williams
Assistant Examiner—David Rogers
(74) Attorney, Agent, or Firm—Leydig, Voit & Mayer, Ltd.

(57) ABSTRACT

The mill comprises a cylindrical shell ring (10) revolving about its longitudinal axis and containing a grinding charge comprising grinding bodies made of metal alloy. At least one grinding body (30) identical to those that make up the grinding charge is fixed to an elastomer or rubber pedestal (28), itself fixed to the interior surface of the shell ring. This grinding body (30) is exposed to the conditions inside the mill and is associated with a reference electrode (36) from which it is electrically insulated. This reference electrode (36) is protected from the impact knocks of the charge in the mill but is in electrical contact with the pulp in the mill, the said grinding body (30) and the said electrode (36) being electrically connected to measurement apparatus (18) fixed inside the shell ring of the mill.

30 Claims, 2 Drawing Sheets

DEVICE FOR DETERMINING THE CORROSION OF THE GRINDING BODIES IN A ROTARY MILL

FIELD OF THE INVENTION

The present invention relates to a device for determining the corrosion of the grinding bodies in a rotary mill comprising a cylindrical shell ring revolving about its longitudinal axis and containing a grinding charge consisting of grinding bodies made of metal alloy, the mill having the material that is to be milled pass longitudinally through it.

BACKGROUND OF THE INVENTION

The invention is aimed more specifically at the field of wet mills, particularly those used in the mining industry for crushing and grinding ores or in the cement-making industry. These mills contain a grinding charge consisting of grinding bodies such as balls, cylindrical pebbles, spherical pebbles, etc., and grinding occurs as the mill rotates under the effect of knocks and friction with the grinding charge and produces a kind of wet pulp.

These grinding bodies experience significant wear and their frequent replacement has a significant impact on the cost of grinding. It is therefore obvious that there is a need to monitor this wear so as to be able to choose appropriate alloys for the grinding bodies and to adapt the running conditions of the mill in order to lengthen the service life of the grinding bodies as far as possible and reduce the running costs of the mills.

Grinding body wear is a complex phenomenon to which essentially mechanical wear and corrosion contribute. Mechanical wear is brought about by abrasion and by the knocks and impacts, while corrosion is an electrochemical phenomenon which occurs in an aqueous medium under the effect of anode and cathode reactions. It is has been found that these various phenomena which are responsible for the overall wear of the grinding bodies have a synergic effect, that is to say that the overall wear is greater than the sum of the wear generated by the various individual phenomena which cause it. In other words, the corrosion of a grinding body which is subjected to mechanical wear may be greater than that of the same grinding body in the absence of mechanical wear, and vice versa.

Until now all that was done about corrosion wear was to observe it and make do with choosing materials and alloys best able to resist it, because there was no means for reliably determining the state and evolution of the corrosion of the grinding bodies while the mill was in operation. This is because the phenomenon of corrosion of the grinding bodies depends on several factors such as the composition and the nature of the alloy of the grinding bodies, the nature of the material being ground (e.g. iron ores or copper ores) the pH of the pulp, etc.

BRIEF SUMMARY OF THE INVENTION

It is an object of the present invention to fill this gap and to provide a device for determining the corrosion of the grinding bodies during the grinding operation which is reliable enough to be able to optimize the grinding conditions and improve the conditions of wear of the grinding charge.

In order to achieve this objective, the present invention provides a device of the kind described in the preamble which is characterized in that at least one grinding body identical to those that make up the grinding charge is fixed to an elastomer or rubber pedestal, itself fixed to the interior surface of the shell ring, and in that this grinding body is exposed to the conditions inside the mill and is associated with a reference electrode from which it is electrically insulated, in that the said reference electrode is protected from impacts and knocks of the charge in the mill but is in electrical contact with the pulp in the mill and in that the said grinding body and the said electrode are electrically connected to measurement apparatus fixed outside the shell ring of the mill.

Each grinding body is preferably fixed to the pedestal and to the shell ring using a hollow bolt passing radially through the pedestal and the shell ring and containing the reference electrode which is bathed in an electrolyte in electrical contact with the pulp in the grinder. The hollow of the bolt may be closed at the interior end by a spongy plug projecting the reference electrode from knocks and allowing contact with the pulp.

The pedestal carrying the grinding bodies and the reference electrodes is preferably fixed on the inside of an inspection hatch, each mill being equipped with at least one of these hatches.

The measurement apparatus makes it possible to measure potential and/or current on each grinding body and its reference electrode and sends the data, telematically, to a receiving module remote from the mill. This module processes and analyses the data, the results of which provide indications regarding the corrosion of the grinding body on which the measurement was made.

BRIEF DESCRIPTION OF THE DRAWINGS

Other specifics and features of the invention will become apparent from the description of a preferred embodiment which is given herein below, by way of illustration, with reference to the appended drawings in which.

DETAILED DESCRIPTION OF THE INVENTION

Figure 1:
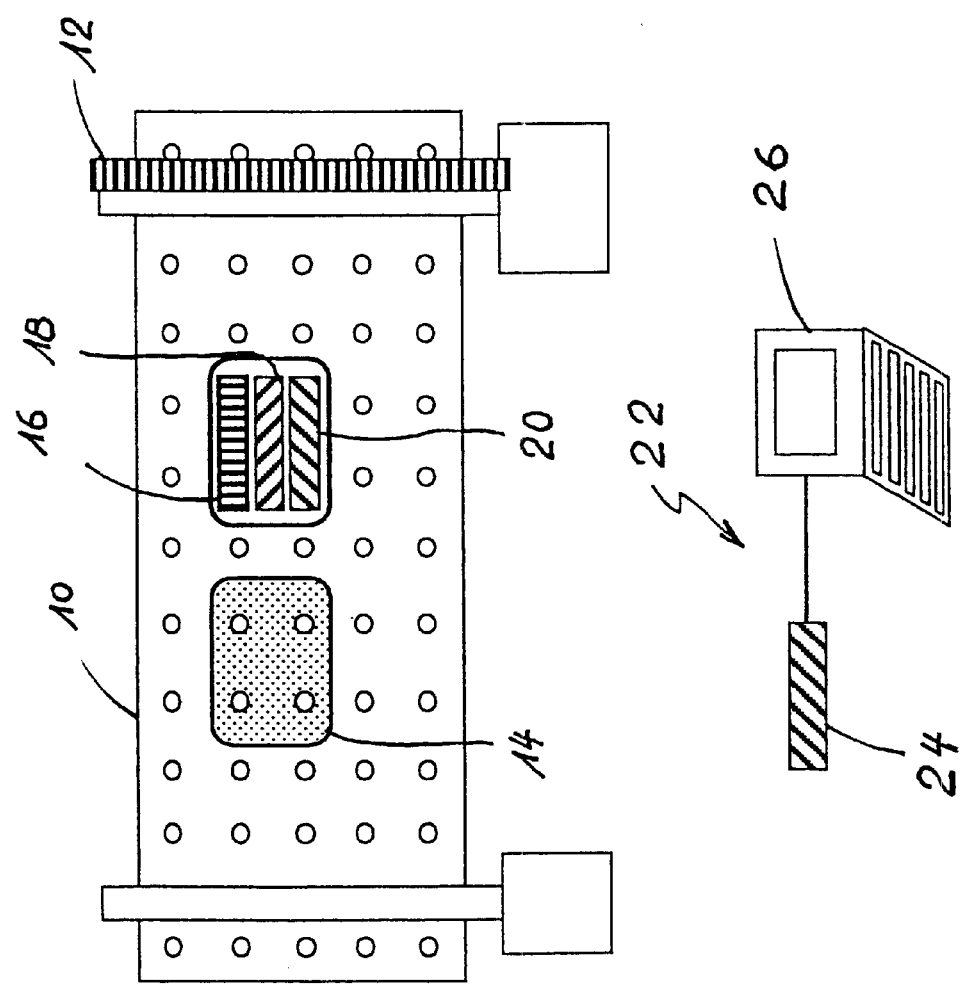
FIG. 1 is a schematic view of the installation as a whole.

FIG. 1, which shows an overview of the installation as a whole, shows the cylindrical shell ring 10 of a tubular mill which revolves about its longitudinal axis and which is supported, at least at its ends, by appropriate bearings, one of which is depicted with the reference 12. The shell ring 10 has at least one inspection hatch 14 which is readily removable and which allows access, if required, to the interior of the mill.

It is beside this hatch 14 that part of the equipment provided by the present invention is fixed, and which therefore revolves, with the shell ring, about the longitudinal axis thereof. It involves, in particular, a source of electrical power 16, preferably a set of batteries, modules 18 for receiving and transmitting measurement data and a means 20 for controlling the measurement operations and which may consist of a remote control.

Remote from this equipment fixed to the shell ring 10 there is a station 22 for processing and analysing the measurement results and which essentially comprises a data reception module 24 and a device 26 for displaying the measurement results. The link between modules 18 and 24 is a telematic link which, as will be seen later on, affords one of the essential advantages of the invention.

Figure 2:
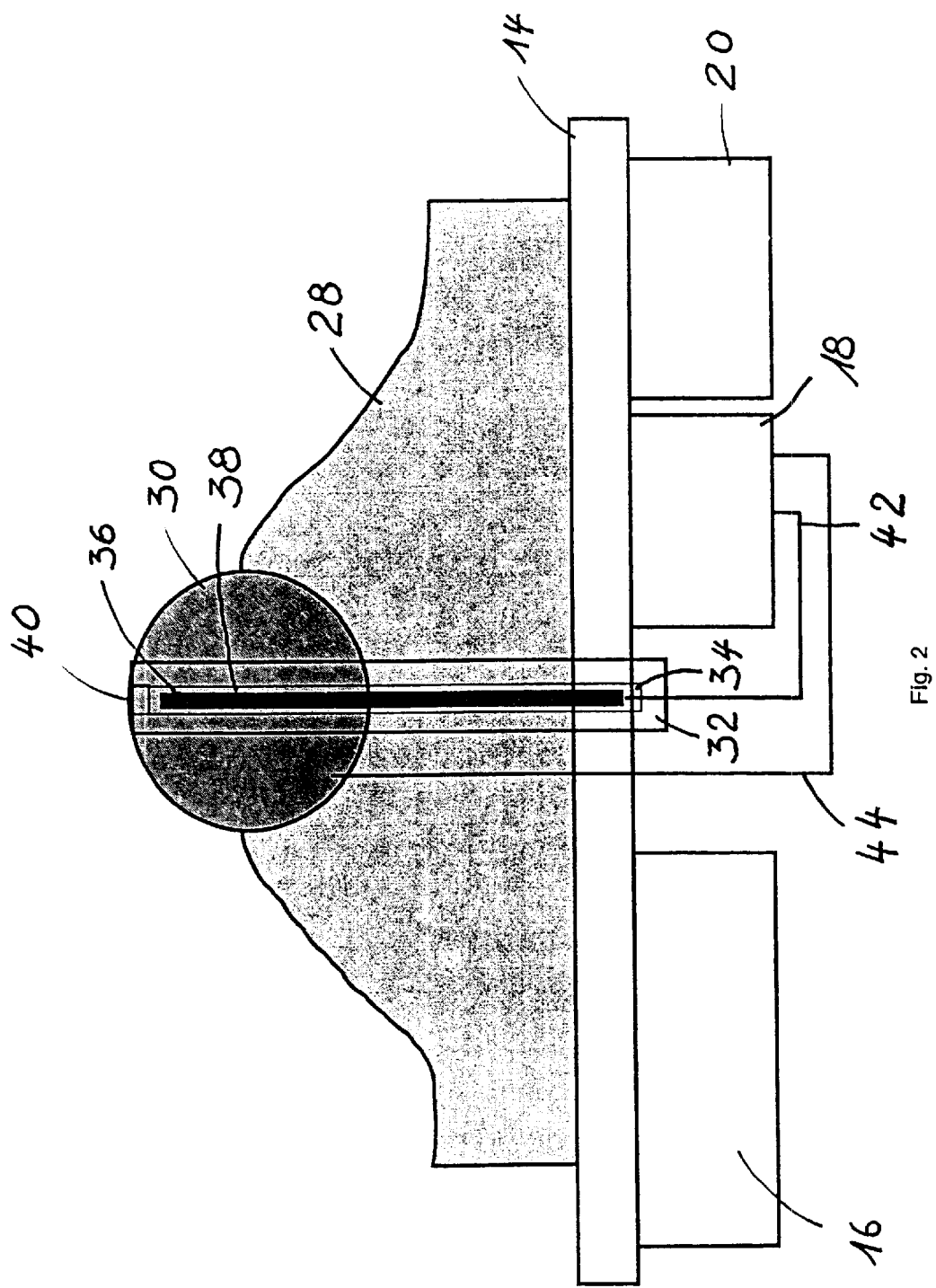
FIG. 2 is a view in cross section through an inspection hatch with a device according to the present invention.

Reference will now be made to FIG. 2 to describe the equipment fixed to and beside the inspection hatch 14. Inside the hatch is fixed a rubber or elastomer pedestal 28 which is oriented in the direction of the generatrix. This pedestal 28 in fact corresponds to the lifters which form part of the interior armouring of a mill and which serve to entrain and stir the contents, that is to say the material that is to be ground, the wet pulp and the grinding charge which, in the example illustrated, consists of grinding balls but which may just as easily consist of grinding bodies of other shapes. The pedestal 28 in its central region comprises a series of juxtaposed cavities, in each of which is housed a grinding ball 30, at least one of which is identical to the balls that make up the grinding charge. These balls 30 are housed in the pedestal in such a way that one of their hemispheres is fixed to the material of the pedestal and the other is exposed to the content of the mill as are the balls that make up the grinding charge.

The balls 30 and the pedestal 28 are fixed to the inspection hatch 14 by bolts 32 passing diametrically through each ball 30 and anchored into these and to the inspection hatch by means which are not shown. Each bolt has an interior axial bore 34 in which there is a calomel reference electrode 36. This electrode 36 is bathed in an electrolyte 38 consisting of a saturated potassium chloride medium and which completely fills the bore 34. This bore 34 is closed towards the inside of the mill by an inert spongy plug 40. The electrode 36 is therefore protected from mechanical influences inside the mill, particularly from the knocks and impacts caused by the charge. By contrast, the electrode 36 is in electrochemical communication, through the plug 40, with the wet pulp inside the mill.

The electrode 36 and the ball 30 are separately in electrical connection, via lines 42 and 44 respectively, with the measurement apparatus 18 fixed on the outside of the inspection hatch 14. This apparatus 18 comprises a reception module and a transmission module which may be of the ADAM type, for example. The line 44 between the ball 30 and the measurement apparatus 18 may also pass through the bolt 32.

The apparatus described hereinabove thus makes it possible to measure the potential difference (in mV) between each ball 30 which is exposed to all the wear factors in the mill and its reference electrode 36. It is also possible to couple two balls made of different alloys and to measure the current (in mA) between these two balls. The data from these measurements are then sent telematically from the transmission module to the reception module 24 which may also be a module of the ADAM type. These data are then processed and analysed by software and the results may be displayed at 26 and printed out. The measurements of the potential at the balls and the electrodes, and of the currents between the various balls short circuited make it possible, by correlation with values obtained by simulation in a laboratory, to obtain information about the corrosion of each of the balls 30 fixed into the pedestal 28, given that at least one of these balls is identical (from the point of view of its nature and its alloy) to the balls that make up the grinding charge and is exposed to the same influences as these. A picture of the effect of the corrosion in the mill is thus obtained directly. It is possible in particular to determine whether the measurement ball in question is in a corrosion zone, to determine the intensity of the corrosion and how it is progressing. Furthermore, if the mill so permits, particularly in the case of those equipped with several inspection hatches, it is possible to provide several measurement stations in the same mill, this making it possible to provide information about corrosion in various parts of the mill.

Transmitting the measurement results telematically makes it possible to perform these measurements online, that is to say directly while grinding is in progress so as to provide as real as possible a picture of the corrosion.

While at least one of the balls 30 has to be the same as those of the grinding charge, it is preferable, in the same pedestal, to provide balls made of a different alloy, harder or softer, etc., as this provides information regarding how different alloys behave under the same operating conditions.

These measurements and this knowledge are therefore useful in optimizing the grinding conditions for the next cycles by tailoring the various parameters and alloys of the grinding bodies to the wear conditions. For example, if it is found that wear by corrosion is low, it might be possible to choose grinding bodies which exhibit better resistance to mechanical wear.

What is claimed is:

1. Device for determining the corrosion of the grinding bodies in a rotary mill comprising a cylindrical shell ring (10) revolving about its longitudinal axis and containing a grinding charge comprising grinding bodies made of metal alloy, the mill having the material that is to be milled pass longitudinally through it, characterized in that at least one grinding body (30) identical to those that make up the grinding charge is fixed to an elastomer or rubber pedestal (28), itself fixed to the interior surface of the shell ring, and in that this grinding body (30) is exposed to the conditions inside the mill and is associated with a reference electrode (36) from which it is electrically insulated, in that the said reference electrode (36) is protected from impact knocks of the charge in the mill that is in electrical contact with the pulp in the mill and in that the said grinding body (30) and the said electrode (36) are electrically connected to a measurement apparatus (18) fixed outside the shell ring of the mill.

2. Device according to claim 1, characterized in that the said pedestal (28) comprises several pairs of grinding bodies (30) and reference electrodes (36), at least one grinding body of which is identical to those that make up the charge.

3. Device according to claim 1, characterized in that each grinding body (30) is fixed to the pedestal (28) and to the shell ring using a hollow bolt (32) passing radially through the pedestal (28) and the shell ring and containing the reference electrode (36).

4. Device according to claim 3, characterized in that the reference electrode (36) is bathed in an electrolyte contained in an axial bore (34) of the bolt (32), the said electrolyte being in electrical contact with the pulp in the mill.

5. Device according to claim 4, characterized in that the axial bore (34) in the bolt (32) is closed, at the interior end, by a spongy plug (40) protecting the reference electrode (36) from knocks and allowing contact with the pulp.

6. Device according to claim 1, characterized in that the pedestal (28) carrying the grinding bodies (30) and the reference electrodes (36) is fixed on the inside of the inspection hatch (14), each mill being equipped with at least one of these hatches.

7. Device according to claim 2, characterized in that the pedestal (28) carrying the grinding bodies (30) and the reference electrodes (36) is fixed on the inside of the inspection hatch (14), each mill being equipped with at least one of these hatches.

8. Device according to claim 3, characterized in that the pedestal (28) carrying the grinding bodies (30) and the reference electrodes (36) is fixed on the inside of the inspection hatch (14), each mill being equipped with at least one of these hatches.

9. Device according to claim 4, characterized in that the pedestal (28) carrying the grinding bodies (30) and the reference electrodes (36) is fixed on the inside of the inspection hatch (14), each mill being equipped with at least one of these hatches.

10. Device according to claim 5, characterized in that the pedestal (28) carrying the grinding bodies (30) and the reference electrodes (36) is fixed on the inside of the inspection hatch (14), each mill being equipped with at least one of these hatches.

11. Device according to claim 1, characterized in that the said measurement apparatus (18) makes it possible to measure potential and current on each grinding body (30) and its reference electrode (36) and sends the data, telematically, to a receiving module (24) remote from the mill.

12. Device according to claim 2, characterized in that the said measurement apparatus (18) makes it possible to measure potential and current on each grinding body (30) and its reference electrode (36) and sends the data, telematically, to a receiving module (24) remote from the mill.

13. Device according to claim 3, characterized in that the said measurement apparatus (18) makes it possible to measure potential and current on each grinding body (30) and its reference electrode (36) and sends the data, telematically, to a receiving module (24) remote from the mill.

14. Device according to claim 4, characterized in that the said measurement apparatus (18) makes it possible to measure potential and current on each grinding body (30) and its reference electrode (36) and sends the data, telematically, to a receiving module (24) remote from the mill.

15. Device according to claim 5, characterized in that the said measurement apparatus (18) makes it possible to measure potential and current on each grinding body (30) and its reference electrode (36) and sends the data, telematically, to a receiving module (24) remote from the mill.

16. Device according to claim 6, characterized in that the said measurement apparatus (18) makes it possible to measure potential and current on each grinding body (30) and its reference electrode (36) and sends the data, telematically, to a receiving module (24) remote from the mill.

17. Device according to claim 7, characterized in that the said measurement apparatus (18) makes it possible to measure potential and current on each grinding body (30) and its reference electrode (36) and sends the data, telematically, to a receiving module (24) remote from the mill.

18. Device according to claim 8, characterized in that the said measurement apparatus (18) makes it possible to measure potential and current on each grinding body (30) and its reference electrode (36) and sends the data, telematically, to a receiving module (24) remote from the mill.

19. Device according to claim 9, characterized in that the said measurement apparatus (18) makes it possible to measure potential and current on each grinding body (30) and its reference electrode (36) and sends the data, telematically, to a receiving module (24) remote from the mill.

20. Device according to claim 10, characterized in that the said measurement apparatus (18) makes it possible to measure potential and current on each grinding body (30) and its reference electrode (36) and sends the data, telematically, to a receiving module (24) remote from the mill.

21. Device according to claim 11, characterized in that the results of the potential and/or current measurements are analysed and correlated with known measurement results so as to provide information regarding the state of corrosion of each ball (30).

22. Device according to claim 12, characterized in that the results of the potential and/or current measurements are analysed and correlated with known measurement results so as to provide information regarding the state of corrosion of each ball (30).

23. Device according to claim 13, characterized in that the results of the potential and/or current measurements are analysed and correlated with known measurement results so as to provide information regarding the state of corrosion of each ball (30).

24. Device according to claim 14, characterized in that the results of the potential and/or current measurements are analysed and correlated with known measurement results so as to provide information regarding the state of corrosion of each ball (30).

25. Device according to claim 15, characterized in that the results of the potential and/or current measurements are analysed and correlated with known measurement results so as to provide information regarding the state of corrosion of each ball (30).

26. Device according to claim 16, characterized in that the results of the potential and/or current measurements are analysed and correlated with known measurement results so as to provide information regarding the state of corrosion of each ball (30).

27. Device according to claim 17, characterized in that the results of the potential and/or current measurements are analysed and correlated with known measurement results so as to provide information regarding the state of corrosion of each ball (30).

28. Device according to claim 18, characterized in that the results of the potential and/or current measurements are analysed and correlated with known measurement results so as to provide information regarding the state of corrosion of each ball (30).

29. Device according to claim 19, characterized in that the results of the potential and/or current measurements are analysed and correlated with known measurement results so as to provide information regarding the state of corrosion of each ball (30).

30. Device according to claim 20, characterized in that the results of the potential and/or current measurements are analysed and correlated with known measurement results so as to provide information regarding the state of corrosion of each ball (30).

* * * * *